US008086336B2

(12) United States Patent  (10) Patent No.: US 8,086,336 B2
Christensen  (45) Date of Patent: Dec. 27, 2011

(54) METHOD FOR DESIGN AND PRODUCTION OF A CUSTOM-FIT PROSTHESIS

(75) Inventor: Andrew M. Christensen, Littleton, CO (US)

(73) Assignee: Medical Modeling Inc., Golden, CO (US)

( * ) Notice: Subject to any disclaimer, the term of this patent is extended or adjusted under 35 U.S.C. 154(b) by 1980 days.

(21) Appl. No.: 10/957,498

(22) Filed: Sep. 30, 2004

(65) Prior Publication Data

US 2005/0133955 A1  Jun. 23, 2005

Related U.S. Application Data

(63) Continuation-in-part of application No. 10/676,661, filed on Sep. 30, 2003, now abandoned.

(60) Provisional application No. 60/437,489, filed on Dec. 31, 2002, provisional application No. 60/414,585, filed on Sep. 30, 2002.

(51) Int. Cl.
*B29C 33/40* (2006.01)
*G06F 19/00* (2011.01)
*B29C 39/08* (2006.01)

(52) U.S. Cl. .......... 700/98; 264/219; 264/227; 264/477; 700/118; 700/119

(58) Field of Classification Search .................. 264/477, 264/219, 227; 700/98, 118, 119
See application file for complete search history.

(56) References Cited

U.S. PATENT DOCUMENTS

| | | | |
|---|---|---|---|
| 4,999,143 A | 3/1991 | Hull et al. | |
| 5,015,424 A | 5/1991 | Smalley | |
| 5,137,662 A | 8/1992 | Hull et al. | |
| 5,167,882 A | 12/1992 | Jacobine et al. | |
| 5,182,715 A | 1/1993 | Vorgitch et al. | |
| 5,184,307 A | 2/1993 | Hull et al. | |
| 5,217,653 A | 6/1993 | Mashinsky et al. | |
| 5,345,391 A | 9/1994 | Hull et al. | |
| 5,370,692 A * | 12/1994 | Fink et al. | 128/898 |
| 5,432,704 A * | 7/1995 | Vouzelaud et al. | 700/182 |
| 5,545,367 A | 8/1996 | Bae et al. | |
| 5,595,703 A | 1/1997 | Swaelens et al. | |

(Continued)

OTHER PUBLICATIONS

Chang et al., "Integration of Design and Manufacturing for Structural Shape Optimization" 2000 pg. Advances in Engineering Software p. 555-567.*

(Continued)

*Primary Examiner* — Albert Decady
*Assistant Examiner* — Thomas H Stevens
(74) *Attorney, Agent, or Firm* — Faegre & Benson LLP

(57) ABSTRACT

Systems and methods are provided for designing and producing a custom-fit prosthesis. According to one embodiment, a mold is produced from which a custom-fit implant may be directly or indirectly manufactured. Medical image data representing surrounding portions of a patient's anatomy to be repaired by surgical implantation of the custom-fit implant are received. Then, three-dimensional surface reconstruction is performed based on the medical image data. Next, the custom-fit implant is designed based on the three-dimensional surface reconstruction and a positive or negative representation of a two-part mold is created with a void in the shape of the custom-fit implant by subtracting a representation of the custom-fit implant from a representation of a mold. Finally, the two-part mold is output from which the custom-fit implant may be directly manufactured; or an implant is directly output. Alternatively, an intermediate mold is created from which a two-part mold may be directly manufactured.

5 Claims, 23 Drawing Sheets

U.S. PATENT DOCUMENTS

| | | | |
|---|---|---|---|
| 5,610,824 A | | 3/1997 | Vinson et al. |
| 5,659,478 A | | 8/1997 | Pennisi et al. |
| 5,665,401 A | | 9/1997 | Serbin et al. |
| 5,741,215 A | | 4/1998 | D'Urso |
| 5,768,134 A | | 6/1998 | Swaelens et al. |
| 5,870,307 A | | 2/1999 | Hull et al. |
| 5,904,889 A | | 5/1999 | Serbin et al. |
| 5,989,476 A | * | 11/1999 | Lockard et al. ............... 264/401 |
| 6,036,910 A | | 3/2000 | Tamura et al. |
| 6,099,787 A | | 8/2000 | Melisaris et al. |
| 6,117,385 A | | 9/2000 | Chartoff et al. |
| 6,136,027 A | * | 10/2000 | Jackson ........................... 623/7 |
| 6,139,574 A | * | 10/2000 | Vacanti et al. ............... 623/1.44 |
| 6,141,889 A | * | 11/2000 | Baum ............................ 36/140 |
| 6,159,411 A | | 12/2000 | Kulkarni et al. |
| 6,207,097 B1 | | 3/2001 | Iverson |
| 6,261,077 B1 | | 7/2001 | Bishop et al. |
| 6,372,173 B1 | | 4/2002 | Peschges |
| 6,399,010 B1 | | 6/2002 | Guertin et al. |
| 6,406,658 B1 | | 6/2002 | Manners et al. |
| 6,600,965 B1 | | 7/2003 | Hull et al. |
| 7,087,200 B2 | * | 8/2006 | Taboas et al. .................... 264/49 |
| 7,117,055 B2 | * | 10/2006 | Mateau et al. ................... 700/98 |
| 7,134,874 B2 | * | 11/2006 | Chishti et al. ................... 433/24 |
| 2001/0018622 A1 | * | 8/2001 | Asano et al. .................... 700/98 |
| 2002/0059049 A1 | * | 5/2002 | Bradbury et al. ............... 703/11 |
| 2002/0188375 A1 | * | 12/2002 | Shioiri et al. ................. 700/200 |
| 2003/0023266 A1 | * | 1/2003 | Borillo et al. ................. 606/200 |
| 2003/0110662 A1 | * | 6/2003 | Gilman et al. .................... 36/43 |

OTHER PUBLICATIONS

Pinilla et al., "Compact Graph Representsation Solid Freeform Fabricatdion (SFF)" 2000, Journal of Manufacturing System 341-354.*

Marcus et al., "Solid Freeform Fabrication Proceedings", 1998, SFF Symposium, University of Texas at Austin, p. 1, 311-318.*

Rock et al., "Distortion Control for P/M-Based Rapid Prototyping of Advanced Material Components", 1996, World Congress on Power Metallurgey and Particulate Materials, 15 pages.*

Bose et al., "Processing of Controlled Porosity Ceramic Structures via Fused Deposition", 1999, Washington State University, p. 1009-1014.*

Wohlers, Terry T., "Wohlers Report 2002, Rapid Prototyping & Tooling State of the Industry Annual Worldwide Progress Report," Wohlers Associates, Inc. 2002, Ft. Collins, Colorado.

Medical Modeling LLC, CT-Based Anatomical Models, 2001 (3 pages), 4 pages.

Medical Modeling LLC, www.medicalmodeling.com (7 pages).

Medical Modeling LLC, Vworks 4.0 Software Specification, Clinic 3D, www.medicalmodeling.com, 2004 (3 pages).

* cited by examiner

1110

1120

1130

METHOD FOR DESIGN AND PRODUCTION OF A CUSTOM-FIT PROSTHESIS

This application is a continuation in part of U.S. application Ser. No. 10/676,661, filed Sep. 30, 2003, entitled "Method for Design and Production of a Custom-Fit Prosthesis;" and claims the benefit of U.S. Provisional Application No. 60/414,585, filed Sep. 30, 2002, entitled "Method for Design and Production of a Custom-Fit Cranioplasty Prosthesis;" and U.S. Provisional Application No. 60/437,489, filed Dec. 31, 2002, entitled "Method for Design and Production of a Custom-Fit Cranioplasty Prosthesis;" each of which is hereby incorporated by reference in its entirety.

COPYRIGHT NOTICE

Contained herein is material that is subject to copyright protection. The copyright owner has no objection to the facsimile reproduction of the patent disclosure by any person as it appears in the Patent and Trademark Office patent files or records, but otherwise reserves all rights to the copyright whatsoever. Copyright© 2002-2004 Medical Modeling, LLC.

BACKGROUND

1. Field

Embodiments of the present invention relate generally to design and production of implants. More particularly, embodiments of the present invention relate to techniques for computer-designed, preformed implants via (i) production of precise molds for direct manufacture of the desired implant; (ii) production of "a mold of a mold" from which a new mold may be formed and used to manufacture the desired implant; (iii) direct production of the desired implant; and/or (iv) delivery of data files representing any of the foregoing.

2. Description of the Related Art

The term cranioplasty refers to the surgical correction of a skull defect. These large defects of the human skull may be created or caused by injury, surgical intervention for tumor removal, congenital abnormality or disease. Many times a repair and recontouring of a defect of this type will involve either autogenous (body tissue) or alloplastic (man-made) materials, but in many cases of large defects there is not enough autogenous material to use for repair. Surgeons in the fields of neurosurgery, oral surgery and plastic surgery repair and recontour these defects using alloplastic materials such as polyethylene, polymethylmethacrylate, tantalum, cobalt-chrome, hydroxyapatite, titanium, and methylmethacrylate (bead or solid form). Currently, most surgeons fixing these defects do so by forming the material at the time of surgery with the patient's anatomy exposed. The current method exposes the patient to longer surgery and often leaves a less than desirable appearance, especially with large defects. Issues of symmetry between the right and left sides of the head and reconstruction of a bilateral defect are difficult to consider when forming the implant during surgery.

BRIEF DESCRIPTION OF THE SEVERAL VIEWS OF THE DRAWINGS

Embodiments of the present invention are illustrated by way of example, and not by way of limitation, in the figures of the accompanying drawings and in which like reference numerals refer to similar elements and in which.

SUMMARY

Figure 1:
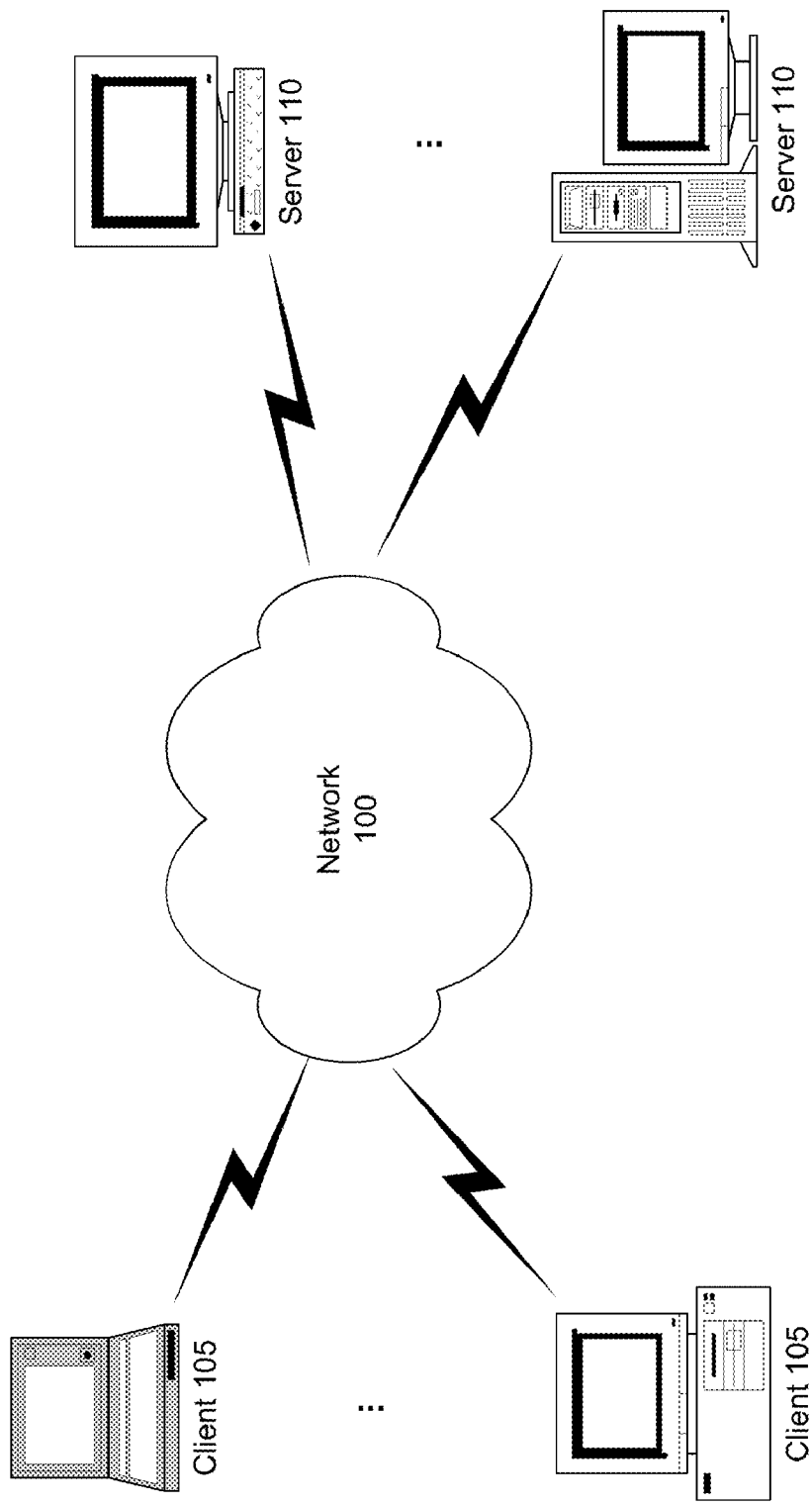
FIG. 1 conceptually illustrates a high-level, simplified view of a network environment in which one embodiment of the present invention may be employed.

Systems and methods for designing and producing a custom-fit prosthesis are described. According to one embodiment, a mold is produced from which a custom-fit implant may be manufactured. Medical image data representing surrounding portions of a patient's anatomy to be repaired by surgical implantation of the custom-fit implant are received. Then, three-dimensional surface reconstruction is performed based on the medical image data. Next, the custom-fit implant is designed based on the three-dimensional surface reconstruction and a two-part mold is created with a void in the shape of the custom-fit implant by subtracting a representation of the custom-fit implant from a representation of a mold. Finally, the two-part mold is output from which the custom-fit implant may be manufactured.

According to another embodiment, an intermediate mold is produced from which a two-part custom-fit implant mold may be manufactured. Medical image data representing surrounding portions of a patient's anatomy to be repaired by surgical implantation of the custom-fit implant are received. Then, three-dimensional surface reconstruction is performed based on the medical image data. Next, the custom-fit implant is designed based on the three-dimensional surface reconstruction and a model of a two-part mold is created with a void in the shape of the custom-fit implant by subtracting a representation of the custom-fit implant from a representation of a mold. Next, a negative model of the two-part mold is created and output to form an intermediate mold from which the two-part custom-fit implant mold may be manufactured. The custom-fit implant may then be manufactured from the two-part custom-fit implant mold.

According to yet another embodiment, a custom-fit implant may be directly produced. Medical image data representing surrounding portions of a patient's anatomy to be repaired by surgical implantation of the custom-fit implant are received. Then, three-dimensional surface reconstruction is performed based on the medical image data. Next, the custom-fit implant is designed based on the three-dimensional surface reconstruction. Finally, the custom-fit implant is output.

Other features of embodiments of the present invention will be apparent from the accompanying drawings and from the detailed description that follows.

DETAILED DESCRIPTION

Systems and methods are described for designing and producing a custom-fit prosthesis. Broadly stated, embodiments of the present invention make use of sophisticated software packages and rapid prototyping processes to facilitate the design and production of preformed implants. According to one embodiment, based upon computer-designed, preformed implants, precise molds are directly produced from which the desired implant may be manufactured. According to another embodiment, "a mold of a mold" (intermediate mold) may be produced from which a new mold may be formed and used to manufacture the desired implant. According to another embodiment, data files representing models of such implants or molds thereof may be delivered to implant manufacturers.

According to one embodiment, results of an outsourced medical modeling service may be provided via an Extranet, a secure portal, a Virtual Private Network (VPN), or other communication infrastructure designed to carry data between or among computers.

In the following description, for the purposes of explanation, numerous specific details are set forth in order to provide a thorough understanding of embodiments of the present invention. It will be apparent, however, to one skilled in the art that embodiments of the present invention may be practiced without some of these specific details. In other instances, well-known structures and devices are shown in block diagram form.

Embodiments of the present invention include various steps, which will be described below. The steps may be performed by hardware components or may be embodied in machine-executable instructions, which may be used to cause a general-purpose or special-purpose processor programmed with the instructions to perform the steps. Alternatively, the steps may be performed by a combination of hardware and software.

Embodiments of the present invention may be provided in whole or in part as a computer program product which may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), and magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments of the present invention may also be downloaded as a computer program product, wherein the program may be transferred from a remote computer to a requesting computer by way of data signals embodied in a carrier wave or other propagation medium via a communication link (e.g., a modem or network connection).

While, for convenience, embodiments of the present invention are described with reference to design and manufacture of custom-fit cranioplasty prostheses, embodiments of the present invention are equally applicable to other implant and prosthesis design and manufacturing scenarios, including dental and other facial implants for reconstruction of the oral and/or maxillofacial region, orthopedic implants and the like.

Terminology

Brief definitions of terms used throughout this application are given below.

The terms "connected" or "coupled" and related terms are used in an operational sense and are not necessarily limited to a direct connection or coupling.

The term "implant" generally refers to a structure or device intended to be surgically implanted, such as a dental implant, a subcutaneous implant, or a prosthesis. Examples of implants include cranioplasty prostheses, facial implants for reconstruction of the oral and/or maxillofacial region, orthopedic implants and the like.

The phrases "in one embodiment," "according to one embodiment," and the like generally mean the particular feature, structure, or characteristic following the phrase is included in at least one embodiment of the present invention, and may be included in more than one embodiment of the present invention. Importantly, such phrases do not necessarily refer to the same embodiment.

If the specification states a component or feature "may", "can", "could", or "might" be included or have a characteristic, that particular component or feature is not required to be included or have the characteristic.

The term "responsive" includes completely or partially responsive.

An "intermediate mold" is a mold from which another mold may be made, or a "mold of a mold," and is a tangible instanciation of a "negative of the mold."

Overview

The method described herein, according to one embodiment of the present invention, allows the surgeon to go into surgery with a computer-designed, preformed implant that is perfectly fitting. The concept is that the patient is exposed to a computed tomography (CT) scan or some other medical imaging modality that allows for the visualization of a defect to be corrected. The 2D images obtained from the CT scan may then be used to visualize on the computer the defect in three dimensions. From this, an implant, e.g., a cranioplasty, is computer designed to recontour and repair the defect. In one embodiment, this cranioplasty is digitally reproduced and subtracted from another object or model, forming a core and cavity mold. The mold may then be output as a positive or a negative using Solid Freeform Fabrication ("SFF") technology (see e.g., Wohlers Report 2002, published by Wohlers Associates, Inc., April 2002, 205 pages, softbound) for injection or forming of an implantable material. Alternatively, the delivery model may include providing data representative of the molds and/or the implant to an implant manufacturer for in-house production of the implant and/or mold by the implant manufacturer.

According to one embodiment, the following steps are part of the new method of design and production of custom-fit implants:

Step 1: The patient gets a CT scan in their local medical imaging facility. Medical image data (e.g., CT or MRI) in two-dimensional format (or another type of surface representation format) is transferred to the laboratory that will be used in designing the implant. This data is typically stored in a medical imaging format that allows for visualization of the anatomy in cross sections, such as a format in accordance with the Digital Imaging and Communications in Medicine (DICOM) Standard defined by a joint committee of the American College of Radiology (ACR) and the National Electrical Manufacturers Association (NEMA).

Step 2: Three-dimensional surface reconstruction of the patient's defect is performed in the computer. Where the implant being designed is a cranioplasty, this three-dimensional representation of the patient's skull anatomy may be output in stereolithography (STL) file format or in other surface representation file formats. The dura mater (brain covering) can also be visualized and output at this stage if needed as part of the implant design process.

Step 3: The STL file(s) or other surface representation files are imported into design software for design of the cranioplasty implant. The design of the implant may be based on the patient's own surrounding anatomy, contralateral (the other side) anatomy, and if needed, other normative skull anatomy. Design of the implant typically is done taking into account the thickness of the surrounding skull to allow for an implant that approximates the individual patient's normal anatomy. The imaged dura mater from the CT scan may also be used as an inner table for the implant. In this manner, an implant may be completely designed in the computer.

Step 4: Once the design of the implant is complete, a "box" is created in the computer. The computer model of the implant is embedded into one side of the box model. The implant is then subtracted from the box, creating a void in the shape of the implant on one side of the box. The box file is smoothed, creating a "parting line" for the eventual mold. A second box is created in the computer and positioned over the top of the first. The implant and the first box are then subtracted from the second box, thus creating a box with a void on one side for the implant and a fit to the first box. When the implant file is now taken away, the box is now a two-part mold with the shape of the implant inside of it. Further circular files can be subtracted from the mold halves to allow for the creation of holes for material injection nozzles, etc. In this manner, a mold may be completely designed in the computer without requiring manual adjustment.

Step 5: Once the mold is completely designed in the computer it is then output using a SFF process either as a positive model or as a negative model. A positive model can be output for direct injection of the implantable material, and thus allowing direct production of an implant from the mold. Alternatively, a negative model of the mold can be output as an intermediate mold to allow for forming of the mold in another material (e.g., silicone, urethane, rubber, etc). Current SFF methods include stereolithography, selective laser sintering, fused deposition modeling, multi-jet modeling and 3D printing. The SFF processes produce a three-dimensional object in a series of two-dimensional layers. The two-dimensional layers are built one on top of another until the object is created. If creating a positive of the mold, the material used is preferably durable enough to allow for injection of the implant material and could be composed of plaster, epoxy resin, acrylic resin, urethane, ABS, stainless steel, a mixture of any of these, or other materials. If creating a negative of the mold, the material used is preferably durable enough to allow for forming of the new mold material and could also be composed of plaster, epoxy resin, acrylic resin, urethane, ABS, stainless steel, a mixture of any of these, or other materials.

Step 6: Once the mold is produced, the implant material is then formed within the mold. For liquid-type implant materials, an injector may be used. For bead-type implant materials, a slurry is created and a large amount of the material is "sandwiched" between both sides of the mold while they are compressed. The implant material may be any implantable material, including, but not limited to, polymethylmethacrylate, bead polymethylmethacrylate, polyethylene, bead polyethylene, cobalt-chrome, titanium, hydroxyapatite, and polytetrafluoroethylene. The implant material is allowed to harden and then is removed from the mold. Minor finishing to the cranioplasty implant may be performed to remove any flash or extra material produced during the injection or forming process.

FIG. 1 conceptually illustrates a high-level, simplified view of a network environment in which one embodiment of the present invention may be employed. In the exemplary client-server environment depicted, such as the World Wide Web (the Web), efficient business-to-consumer or business-to-business communication and commerce may take place. The architecture of the Web follows a conventional client-server model. The terms "client" and "server" are used to refer to a computer's general role as a requester of data (the client) or provider of data (the server). Web clients 105 and Web servers 110 communicate using a protocol such as HyperText Transfer Protocol (HTTP). In the Web environment, Web browsers reside on clients and render Web documents (pages) served by the Web servers. The client-server model is used to communicate information between clients 105 and servers 110. Web servers 110 are coupled to a communications network, such as the Internet 100, and respond to document requests and/or other queries from Web clients 105. When a user selects a document by submitting its Uniform Resource Locator (URL), a Web browser, such as Netscape Navigator or Internet Explorer, opens a connection to a server 110 and initiates a request (e.g., an HTTP get) for the document. The server 110 delivers the requested document, typically in the form of a text document coded in a standard markup language such as HyperText Markup Language (HTML).

According to one embodiment, client 105 and server 110 systems may include various parties involved in the capture of medical imaging data, prosthesis design, prosthesis development, prosthesis manufacturing, and/or prosthesis implantation processes, such as medical imaging services/sources, custom prosthesis developers, implant manufacturers, surgeons, model makers, and others.

In one embodiment, medical imaging data may be provided from a remote medical imaging system to a custom prosthesis developer. Subsequently, refinement, verification and/or delivery of data files representative of models of a target prosthesis, the surrounding bone structure, molds of the target prosthesis, or the like may be performed by secure online interactions among the relevant parties' computer systems and databases. For example, clients 105 and servers 110 may communicate by way of a dial up connection, digital subscriber line (DSL) service, cable modem, integrated services digital network (ISDN) service, wireless service provider (WSP) or other internet service provider (ISP), for example.

According to one embodiment, the network 100 is a private communications network, such as a LAN (e.g., an Ethernet LAN or a token ring LAN), an Intranet, an Extranet, a VPN, or any other communication structure designed to carry data between a plurality of computers associated with a particular enterprise or organization. The network 100 may consist of many inter-linked LANs and/or leased lines in a wide area network (WAN) or the Internet. According to another embodiment, the network 100 is a public communications network, such as a WAN, an Extranet or the Internet. Additionally, according to one embodiment, the communication links among the clients 105, servers 110, and network 100 may be secured or encrypted using conventional web protocols, such as Secure HTTP (S-HTTP), Secure Sockets Layer (SSL), or the like.

Figure 2:
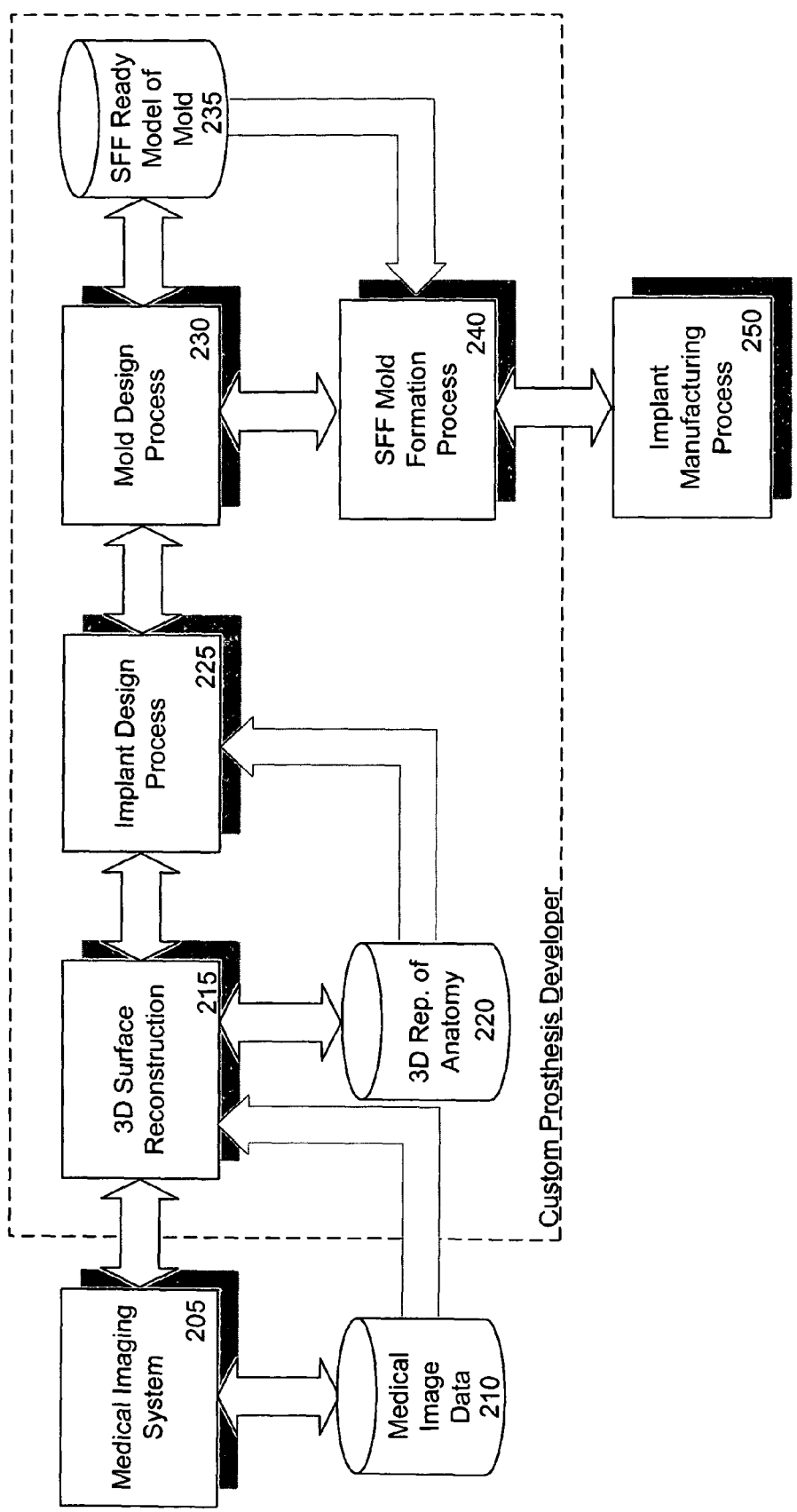
FIG. 2 is a block diagram that conceptually illustrates a custom prosthesis development system according to a first embodiment of the present invention in which a final mold from which an implant may be directly manufactured or data files representative thereof may be delivered to an implant manufacturer.

FIG. 2 is a block diagram that conceptually illustrates a custom prosthesis development system according to a first embodiment of the present invention in which the final mold from which the implant may be directly manufactured or data files representative thereof may be delivered to an implant manufacturer. Medical image data 210 is collected via a CT scan or some other medical imaging modality that allows for the visualization of a defect to be corrected. A medical imaging system 205 may be used to visualize the medical image data 210 on the computer to see the defect in three dimensions. Using the medical image data 210 or the medical imaging system 205 representation, a three-dimensional virtual surface reconstruction 215 can be made. Data pertaining to a three-dimensional representation of the patient's anatomy 220 may also be used and/or created in the three-dimensional surface reconstruction 215. The three-dimensional representation of the patient's anatomy 220 and the three-dimensional surface reconstruction 215 are then imported into design software to begin the implant design process 225. The implant may be completely designed in the computer. The design of the implant may take into account the thickness of the surrounding anatomy to allow for an implant that approximates the individual patient's normal anatomy.

Once the implant design process 225 is complete, the mold design process 230 begins. During this process, a virtual "box" is created in the computer. The computer model of the implant is embedded into one side of the box model. The implant is then subtracted from the box, creating a void in the shape of the implant on one side of the box. The box file is smoothed, creating a "parting line" for the eventual mold. A second box is created in the computer and positioned over the top of the first. The implant and the first box are then subtracted from the second box, thus creating a box with a void on one side for the implant and a fit to the first box. When the implant file is taken away, the box is now a two-part mold with the shape of the implant inside of it. Further conical or circular files can be subtracted from the mold halves to allow for the creation of holes for material injection nozzles. Through the mold design process, a SFF ready model of the mold 235 is created.

Next, according to the present example, a SFF mold formation process 240 is used to output a three-dimensional rendering of the SFF ready model 235 of the mold. A positive model of the mold is output for the SFF mold formation process 240, which creates a three-dimensional tangible mold by building a series of two-dimensional layers one on top of another. The custom prosthesis developer may then send the mold to a customer or manufacturer or other end-user, who may then conduct the implant manufacturing process 250 by injection or compression of implant material within the mold.

As seen in one embodiment of FIG. 2, medical image data 210 may be sent to a custom prosthesis developer through a separate medical imaging system 205 entity. Alternatively, the custom prosthesis developer may receive directly from an outside source a three-dimensional surface reconstruction 215 and/or a three-dimensional representation of the patient's anatomy 220 on which to base the implant design process 225. Alternatively, the custom prosthesis developer may receive directly from an outside source a representation of the implant on which to base the mold design process 230. As yet another embodiment, the custom prosthesis developer may send a SFF file representation of the mold directly to a customer, end-user, or manufacturer to allow the SFF mold formation process 240 and implant manufacturing process 250 to occur off-site.

Figure 3:
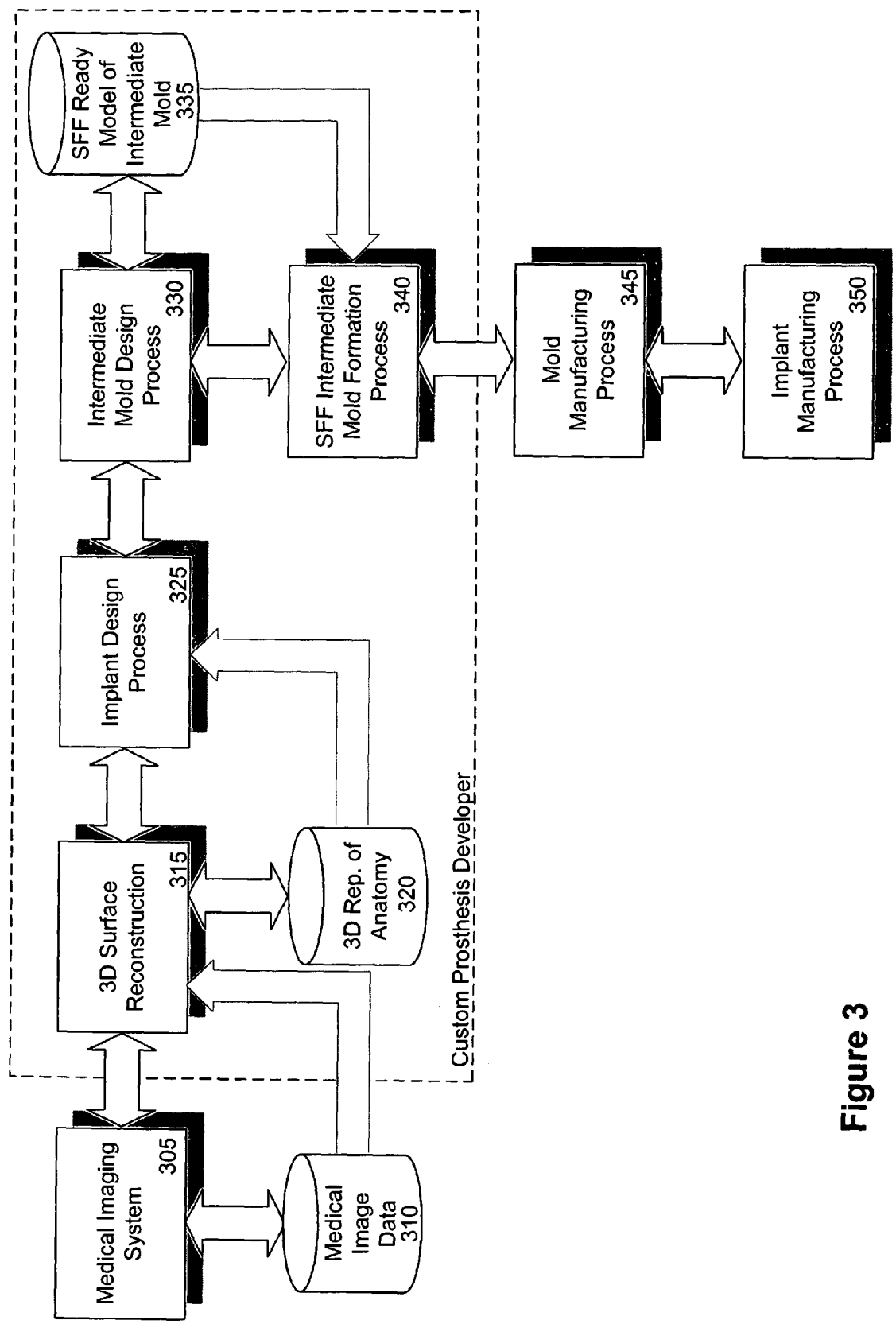
FIG. 3 is a block diagram that conceptually illustrates a custom prosthesis development system according to a second embodiment of the present invention in which "a mold of a mold," or intermediate mold, from which a final mold may be manufactured or data files representative thereof may be delivered to an implant manufacturer.

FIG. 3 is a block diagram that conceptually illustrates a custom prosthesis development system according to a second embodiment of the present invention in which "a mold of a mold" (intermediate mold) from which the final mold may be manufactured or data files representative thereof may be delivered to an implant manufacturer. Similarly to the first embodiment shown in FIG. 2, medical image data 310 is collected via a CT scan or some other medical imaging modality that allows for the visualization of a defect to be corrected. A medical imaging system 305 may be used to visualize the medical image data 310 on the computer to see the defect in three dimensions. Using the medical image data 310 or the medical imaging system 305 representation, a three-dimensional virtual surface reconstruction 315 can be made. Data pertaining to a three-dimensional representation of the patient's anatomy 320 may also be used and/or created in the three-dimensional surface reconstruction 315. The three-dimensional representation of the patient's anatomy 320 and the three-dimensional surface reconstruction 315 are then imported into design software to begin the implant design process 325.

Once the implant design process 325 is complete, the intermediate mold design process 330 begins. Through the intermediate mold design process, a SFF ready model 335 of the intermediate mold is created. Next, unlike the SFF process 240 of the embodiment described with reference to FIG. 2, the SFF intermediate mold formation process 340 in accordance with the present example outputs the intermediate mold, which is an instanciation of a negative model of the mold. This intermediate mold is a "mold of a mold" (a mold from which a final mold may be produced). The intermediate model output from the SFF process 340 may be sent by the custom prosthesis developer to a customer, end-user, or manufacturer. The customer or manufacturer conducts the mold manufacturing process 345 to create a final two-part mold. Once the mold has been produced, the implant manufacturing process 350 may be conducted using the mold.

As with the system of FIG. 2, the "Custom Prosthesis Developer" may include varying subparts of the system, such that the custom prosthesis developer's system includes elements 325, 330, 335, and 340. For instance, the custom prosthesis developer could additionally conduct the mold manufacturing process 345 after the SFF intermediate mold formation process 340, and send the mold directly to a customer, end-user, or manufacturer for the implant manufacturing process 350.

Figure 4:
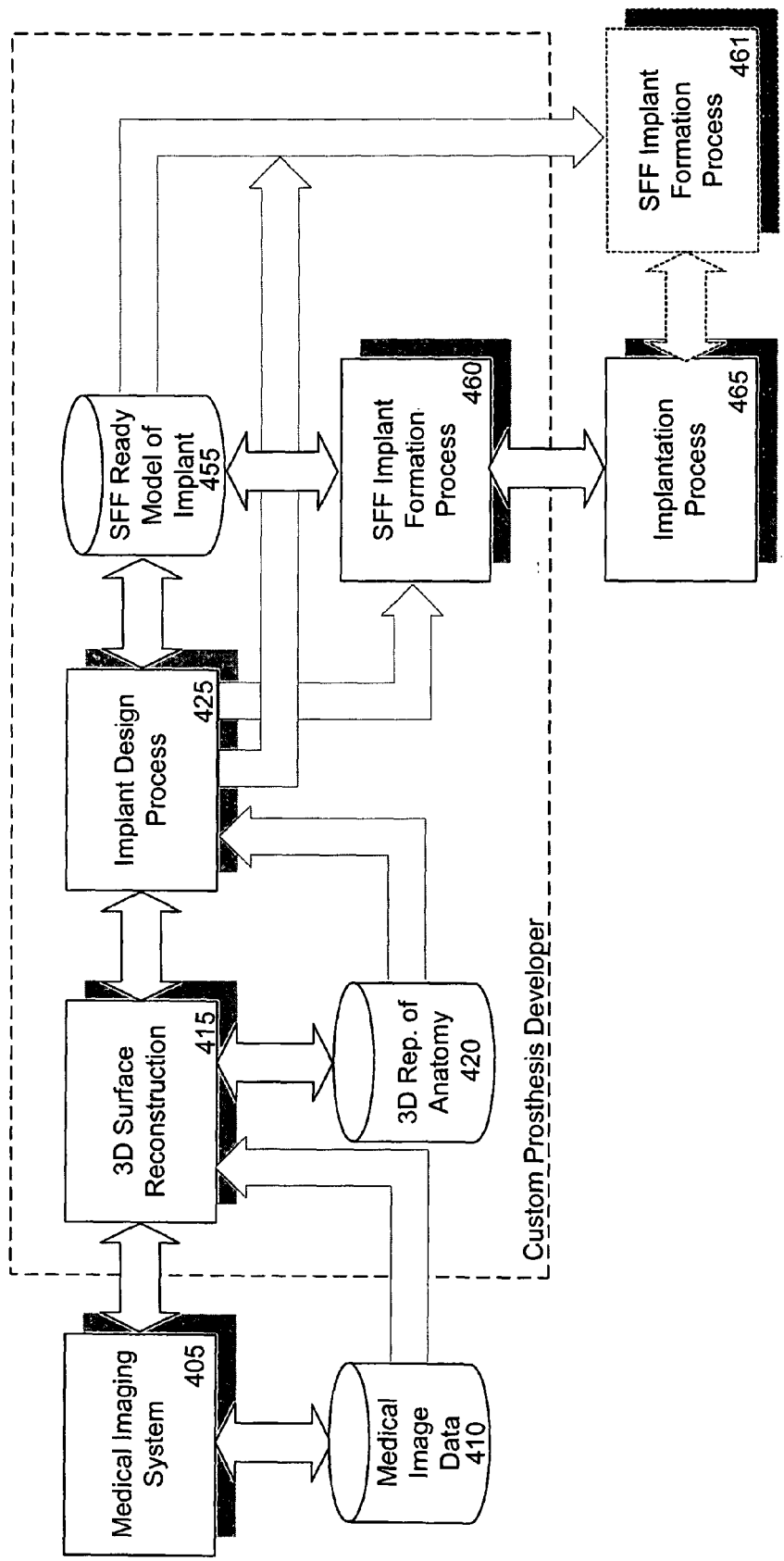
FIG. 4 is a block diagram that conceptually illustrates a custom prosthesis development system according to a third embodiment of the present invention in which an implant or data files representative thereof may be delivered.

FIG. 4 is a block diagram that conceptually illustrates a custom prosthesis development system according to a third embodiment of the present invention in which the implant or data files representative thereof may be delivered. Medical image data 410 is collected via a CT scan or some other medical imaging modality that allows for the visualization of a defect to be corrected. A medical imaging system 405 may be used to visualize the medical image data 410 on the computer to see the defect in three dimensions. Using the medical image data 410 or the medical imaging system 405 representation sent to a custom prosthesis developer, a three-dimensional virtual surface reconstruction 415 can be made. Data pertaining to a three-dimensional representation of the patient's anatomy 420 may also be used and/or created in the three-dimensional surface reconstruction 415. The three-dimensional representation of the patient's anatomy 420 and the three-dimensional surface reconstruction 415 are then imported into design software to begin the implant design process 425.

Through the implant design process 425, a SFF ready model of the implant 455 is created. This SFF ready model of the implant may be used by the custom prosthesis developer to conduct the SFF implant formation process 460. The custom prosthesis developer may then send a formed implant to a customer or end user, who subsequently undertakes the implantation process 465. Alternatively, the custom prosthesis developer could deliver to a customer or end-user or manufacturer the data files representative of the SFF ready model of the implant 455, to allow the customer or manufacturer to conduct its SFF own implant formation process 461 prior to the implantation process 465.

Figure 5:
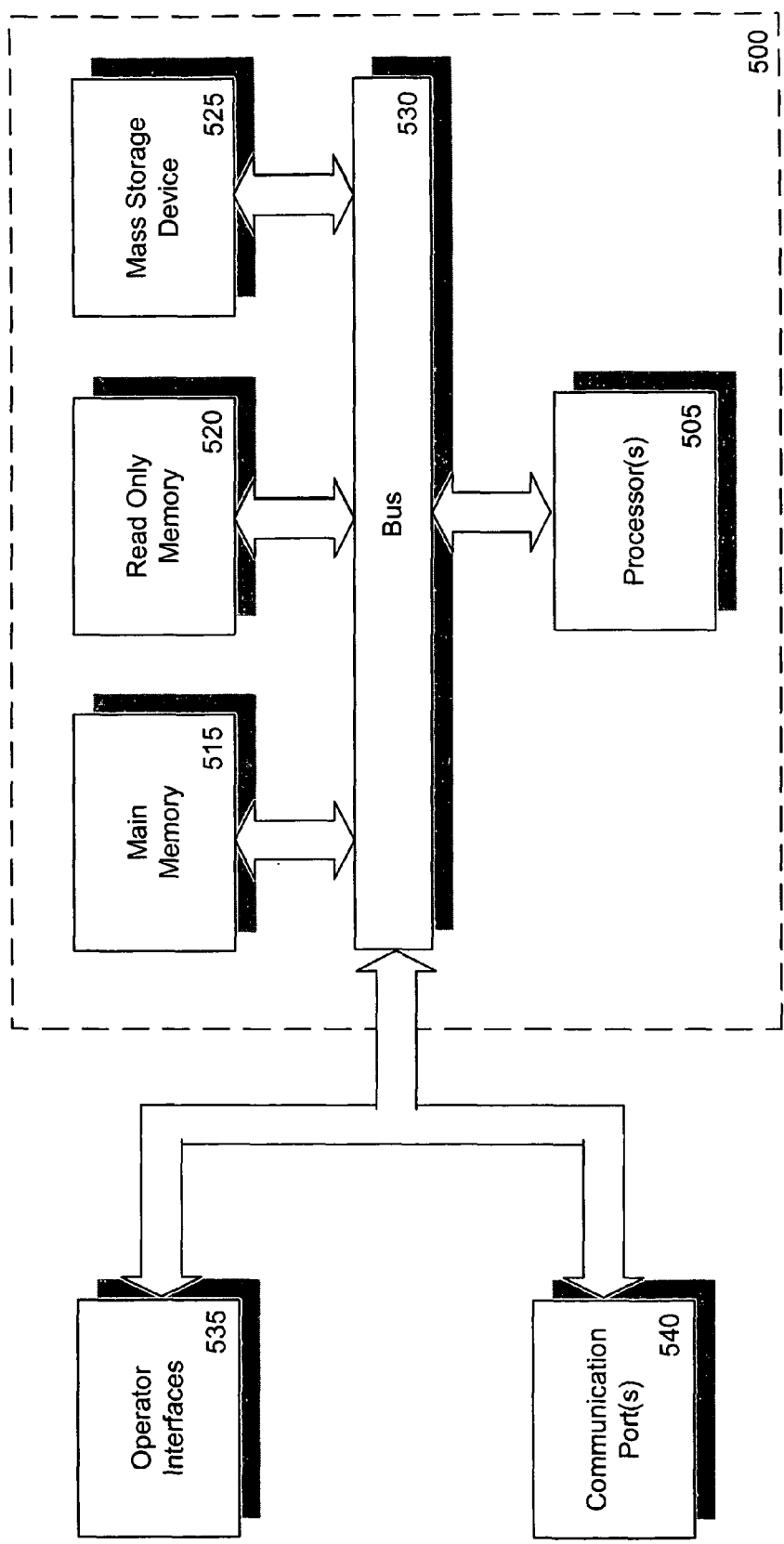
FIG. 5 is an example of a computer system upon which one embodiment of the present invention may be implemented.

An exemplary computer system 500, representing an exemplary application server, web server, or database server, in which features of the present invention may be implemented will now be described with reference to FIG. 5. In this simplified example, the computer system 500 comprises a bus 530 or other communication means for communicating data and control information, and one or more processors 505, such as SPARC® processors, PowerPC G4 processors, Intel® Pentium®, Itanium® or Itanium 2 processors or the like, coupled with bus 530.

Computer system 500 further comprises a random access memory (RAM) or other dynamic storage device (referred to as main memory 515), coupled to bus 530 for storing information and instructions to be executed by processor(s) 505. Main memory 515 also may be used for storing temporary variables or other intermediate information during execution of instructions by processor(s) 515.

Computer system 500 also comprises a read only memory (ROM) 520 and/or other static storage device coupled to bus 530 for storing static information and/or instructions for processor(s) 505.

A mass storage device 525, such as a magnetic disk or optical disc and its corresponding drive, may also be coupled to bus 530 for storing information and instructions, such as an operating system, a web server, a relational database management system (RDBMS), initialization files, etc.

Computer system 500 may also include operator interfaces 535, such as a display, keyboard, and other user input devices (not shown) for allowing an operator to interact with the computer system 500 and/or provide maintenance, monitoring, or support services.

One or more communication ports 540 may also be coupled to bus 530 for supporting network connections and communication of information to/from the computer system 500 by way of a LAN, WAN, the Internet, or the public switched telephone network (PSTN), for example. The communication ports 540 may include various combinations of well-known interfaces, such as one or more modems to provide dial up capability, one or more 10/100 Ethernet ports, one or more Gigabit Ethernet ports (fiber and/or copper), or other well-known network interfaces commonly used in internetwork environments. In any event, in this manner, the computer system 500 may be coupled to a number of other network devices, clients and/or servers via a conventional network infrastructure, such as an enterprise's Intranet and/or the Internet, for example.

Figure 6:
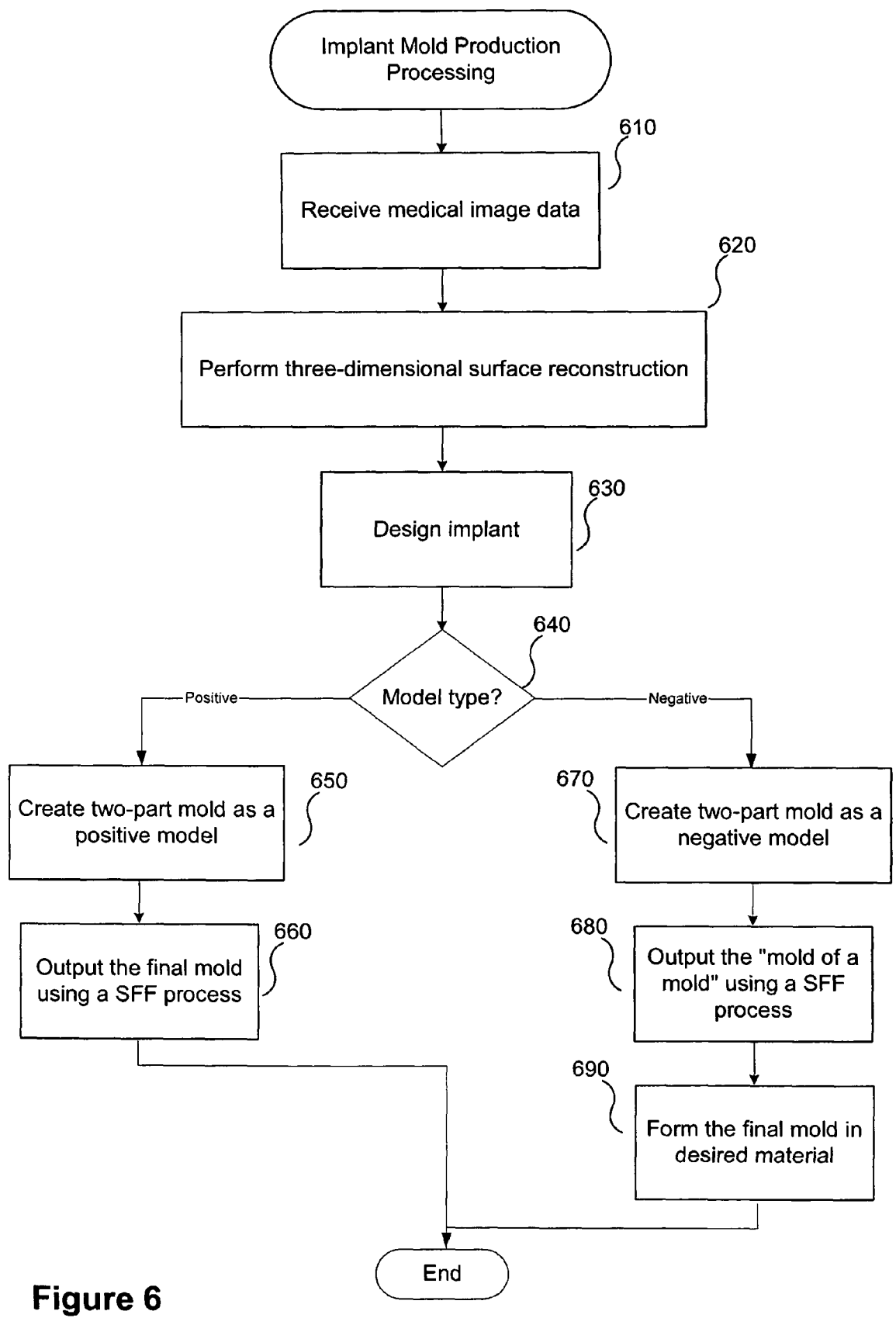
FIG. 6 is a flow diagram illustrating the design and production of a final mold from which a custom-fit prosthesis may be directly manufactured according to one embodiment of the present invention.

FIG. 6 is a flow diagram illustrating the design and production of a final mold from which a custom-fit prosthesis may be directly manufactured according to one embodiment of the present invention. According to one embodiment, in order to produce an implant mold, a first step 610 is to receive the medical image data corresponding to a patient's anatomy. This medical image data may be two-dimensional data, such as CT or MRI image data, or another type of surface representation data. In a next step, at block 620, a three-dimensional surface reconstruction is performed. Using the three-dimensional surface reconstruction, at block 630 the custom prosthesis developer then designs the implant. This design of the implant may be fully automated. This design of the implant may also involve manual input from a design technician using design software to manipulate the models of the prosthesis and of the two-part mold to best conform to the three-dimensional surface reconstruction and the patient's existing anatomy (including surrounding, contralateral, or normative anatomy). At block 640, a next step is to determine which model type to output. At block 650, a two-part mold may be created as a positive model, which leads to block 660: outputting the final mold using a SFF process. Or, alternatively, at block 670 a two-part mold may be created as a negative model in order to output, at block 680, the "mold of a mold" (intermediate mold) using a SFF process. Outputting the intermediate mold using a SFF process allows the final mold to be formed, at block 690, in a desired material. In this way, FIG. 6 depicts a process that may be used to create a final mold for an implant, by either directly creating the mold through a SFF process, block 660, or by creating an intermediate mold from which the final mold for an implant can be created, block 680.

Figure 7:
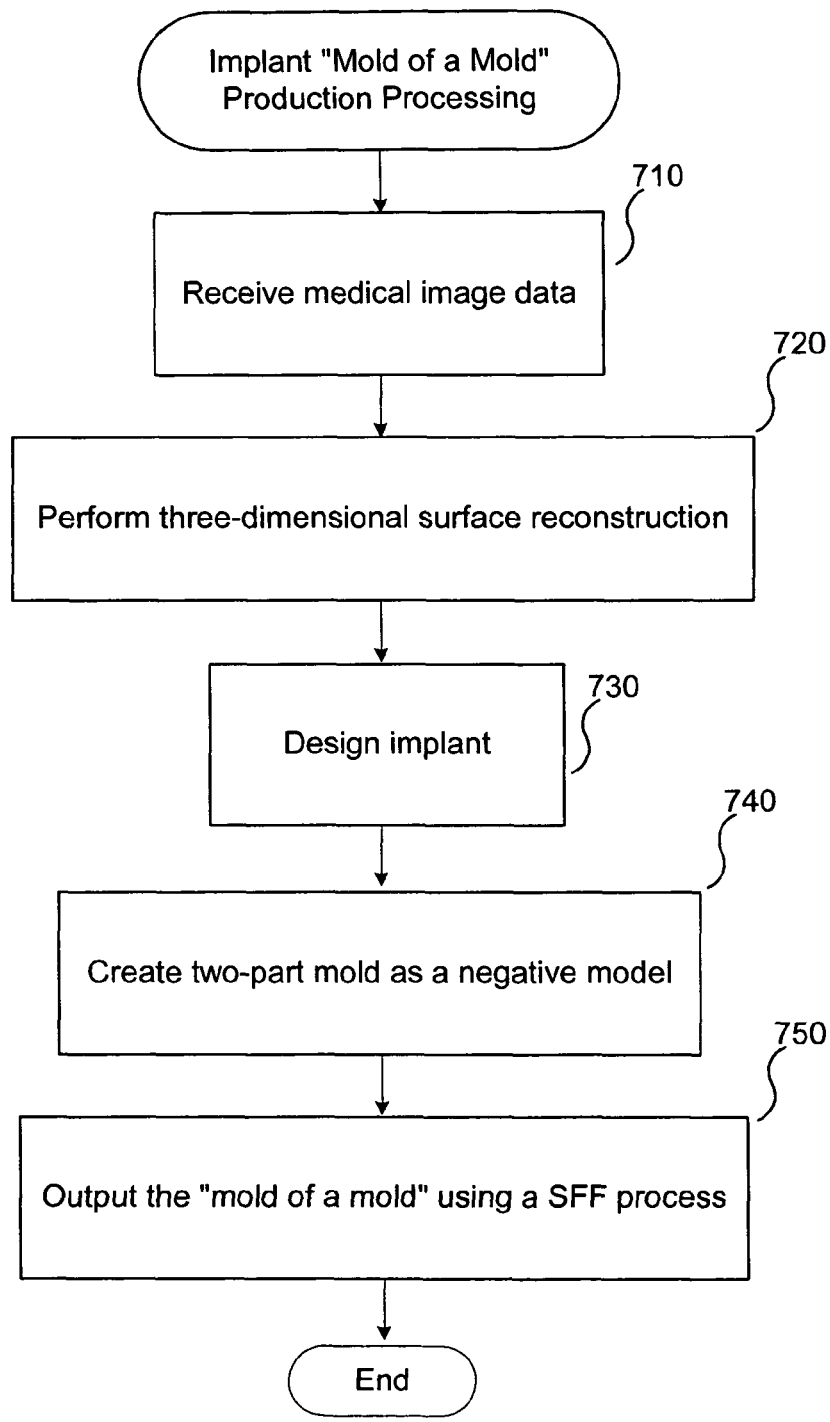
FIG. 7 is a flow diagram illustrating the design and production of "a mold of a mold" from which a final mold for the desired implant may be manufactured according to one embodiment of the present invention.

FIG. 7 is a flow diagram illustrating the design and production of "a mold of a mold" from which a final mold for the desired implant may be manufactured according to one embodiment of the present invention. According to one embodiment, in order to produce an intermediate mold, or a "mold of a mold," a first step 710 is to receive the medical image data corresponding to relevant anatomy of a patient. This medical image data may be two-dimensional data, such as CT or MRI image data. This medical image data may also be composed of other forms or representations of data, including three-dimensional data. This medical image data may also be another form voxel-based volumetric data, which includes information about the x and y pixel size as well as the distance z between images. In a next step, a three-dimensional surface reconstruction is performed 720. Using the three-dimensional surface reconstruction, the custom prosthesis developer then, at block 730, designs the implant. At block 740, a two-part mold may be created as a negative model, which leads to outputting the "mold of a mold" (intermediate mold) using a SFF process 750. In this way, FIG. 7 depicts a process that may be used to create an intermediate mold or, in other words, a "mold of a mold" from which the final mold for an implant can be created.

Figure 8:
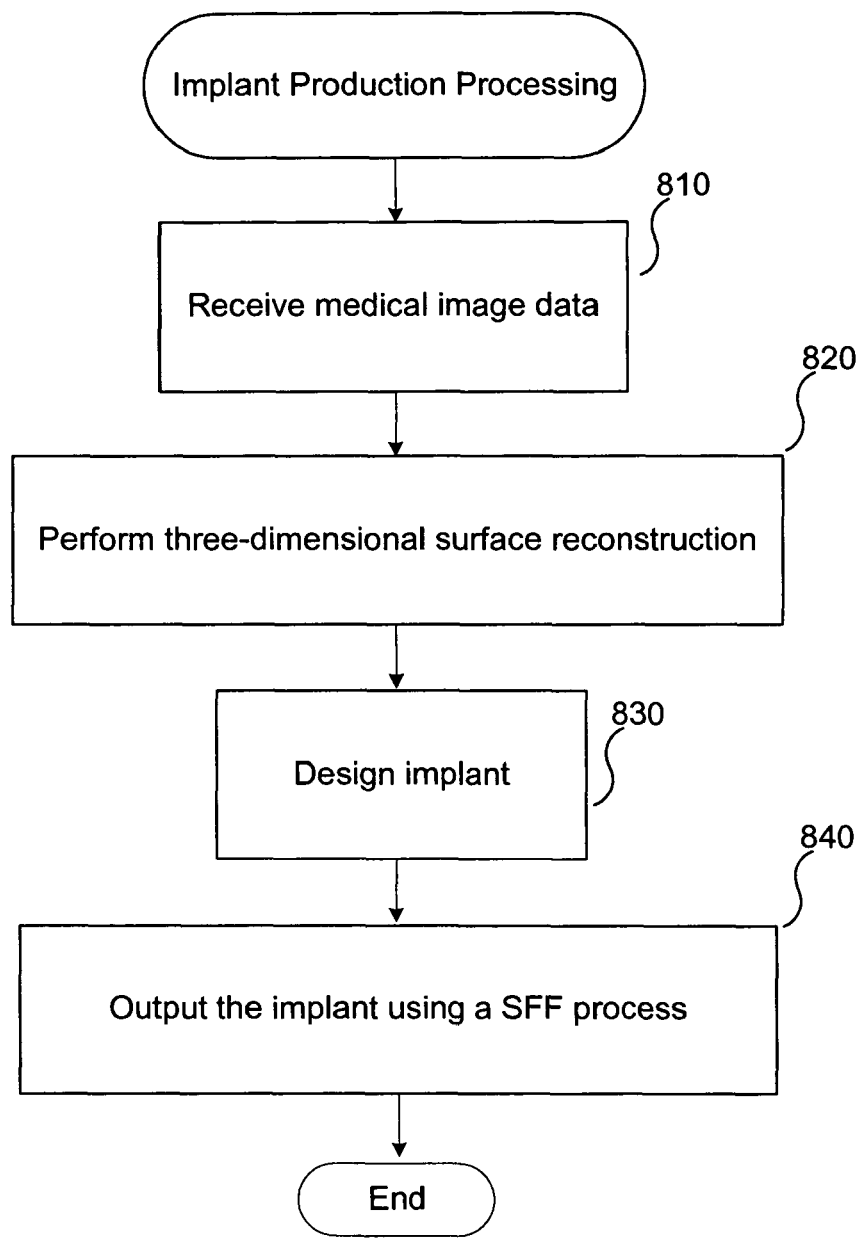
FIG. 8 is a flow diagram illustrating the direct design and production of a custom-fit prosthesis according to one embodiment of the present invention.

FIG. 8 is a flow diagram illustrating the direct design and production of a custom-fit prosthesis according to one embodiment of the present invention. In order to produce an implant, a first step 810 is to receive the medical image data corresponding to a patient's anatomy. This medical image data may be two-dimensional data, such as CT or MRI image data, or another type of surface representation data. In a next step 820, a three-dimensional surface reconstruction is performed. Using the three-dimensional surface reconstruction, the custom prosthesis developer then designs the implant, at block 830. Finally, at block 840, the implant is outputted using a SFF process. In this way, FIG. 8 depicts a process that may be used to either directly create an implant or to output a SFF implant file that contains the blueprint for directly creating the implant. In another embodiment, the same method can be used to produce a mock prosthesis to allow a surgeon to visualize, before surgery, the implant procedure or the geometry of the implant itself. In another embodiment, a surgeon can use a client 105 workstation connected to network 100 to obtain a three-dimensional representation of a patient's anatomy 220, 320, 420 or a SFF ready model of a mold 235, an intermediate mold 335, or implant 455, from a custom prosthesis developer server 110.

Figure 9:
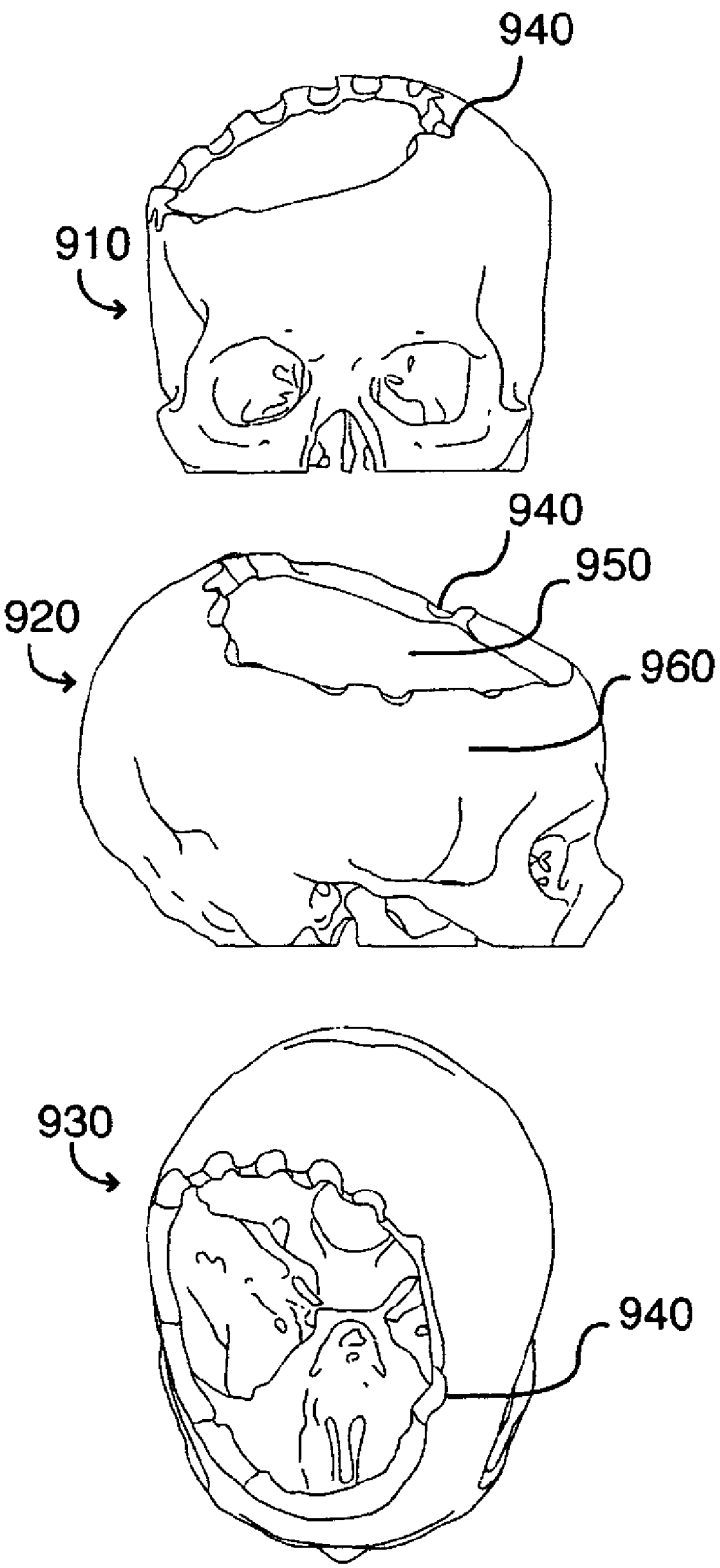
FIG. 9 illustrates a skull with a large bony defect in the right frontal-parietal area, a full-thickness defect resultant from previous surgery.

FIG. 9 illustrates a skull with a large bony defect in the right frontal-parietal area. This is a full-thickness defect resultant from previous surgery. A front view 910, side view 920, and top view 930 are presented. As described above, the medical image data 210, 310, and 410 (as well as the step of receiving medical image data 610, 710, 810), comprises information (and receiving information) representing a patient's defect, such as information about bone surface irregularities 940, the inside surface structure of the skull 950, and the outside surface structure of the skull 960. This information may be used to design the implant depicted in FIG. 10.

Figure 10:
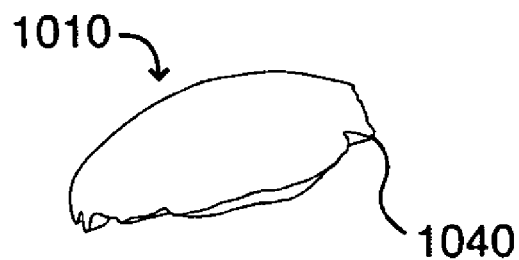
FIG. 10 illustrates a cranioplasty implant by itself.
Figure 10:
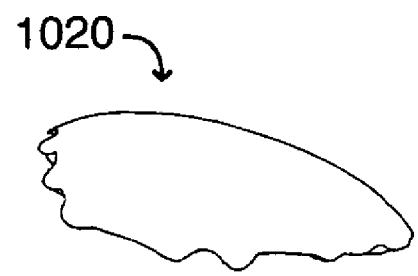
Figure 10:
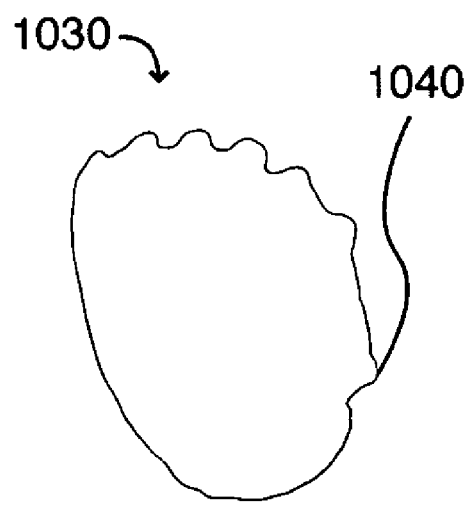

FIG. 10 illustrates a cranioplasty implant by itself. A front view 1010, side view 1020, and top view 1030 are presented. Using one or more embodiments of the present invention, the implant surface 1040 may be designed so that the implant surface 1040 interfaces relatively seamlessly and smoothly with the surface irregularities 940 of the skull.

Figure 11:
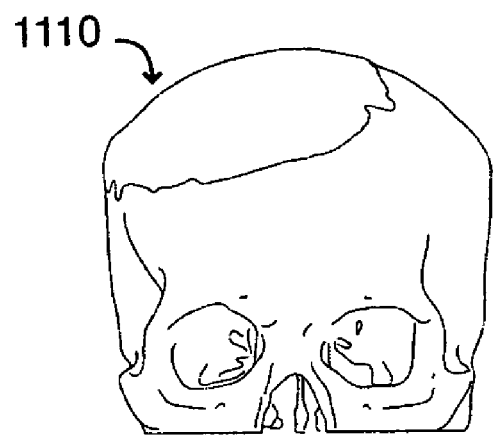
FIG. 11 illustrates a design of a cranioplasty implant in place on the skull meant to repair and reshape the missing bone.
Figure 11:
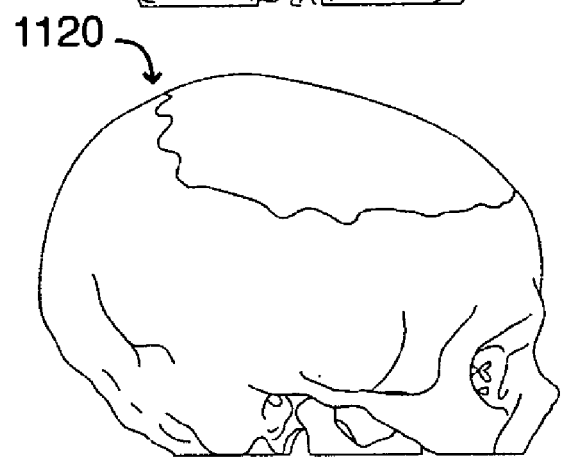
Figure 11:
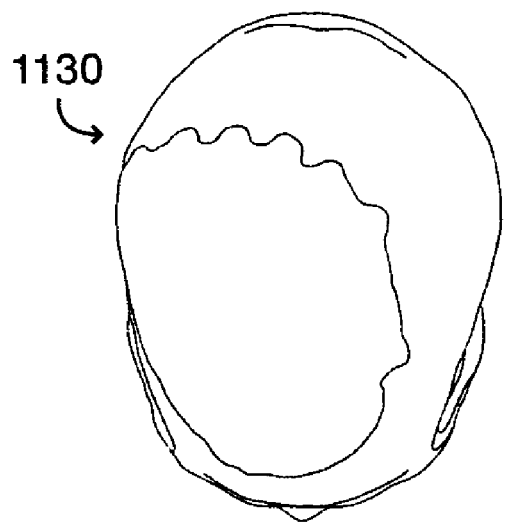

FIG. 11 illustrates a design of a cranioplasty implant in place on the skull meant to repair and reshape the missing bone. A front view 1110, side view 1120, and top view 1130 are presented. The implant surface 1040 interfaces relatively seamlessly and smoothly with the surface irregularities 940 of the skull.

Figure 12:
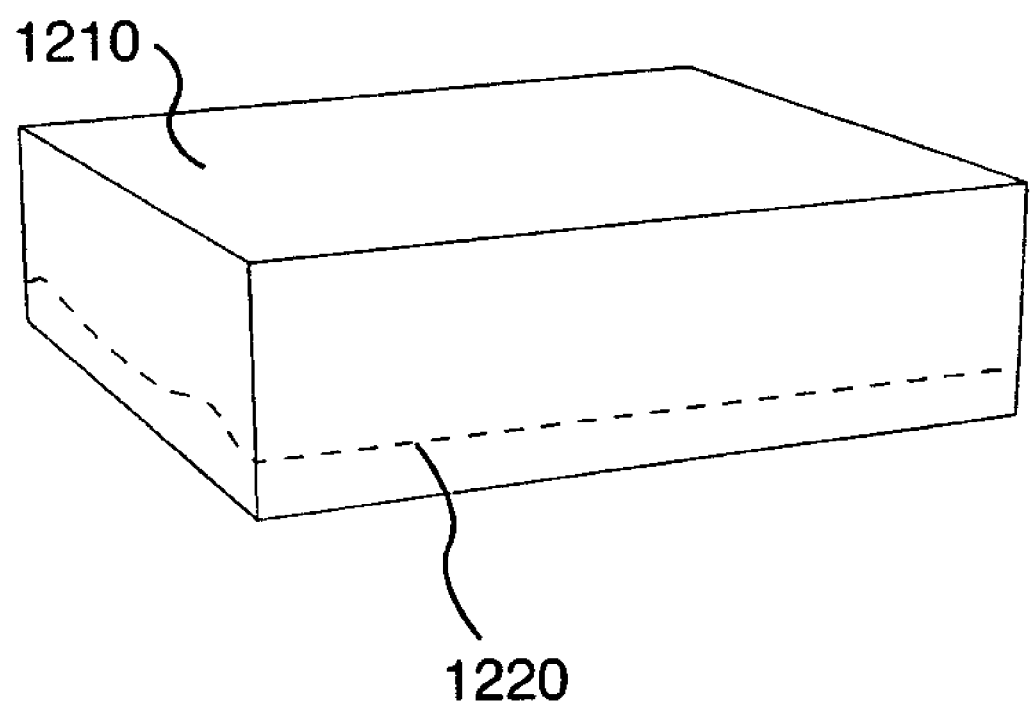
FIG. 12 illustrates a simple block model out of which the finished mold may be designed according to one embodiment of the present invention
Figure 13:
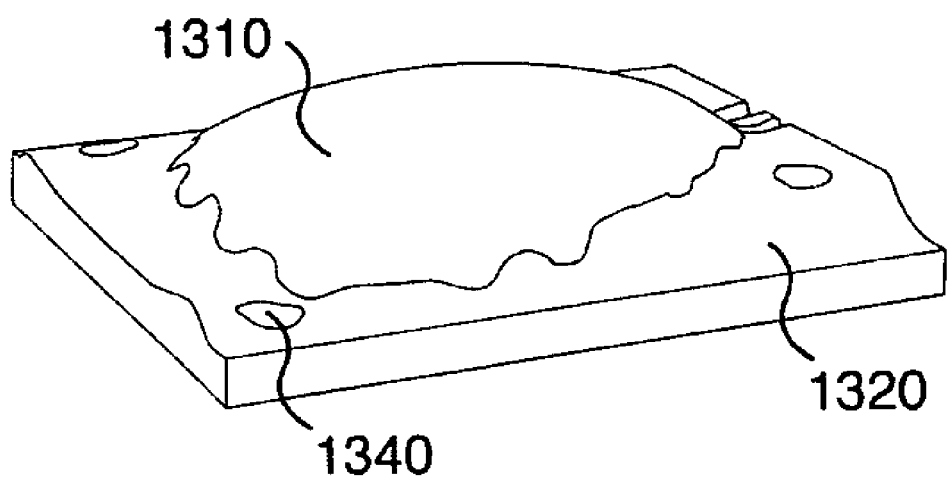
FIG. 13 illustrates an implant embedded into one half of the block that will become the mold according to one embodiment of the present invention.
Figure 14:
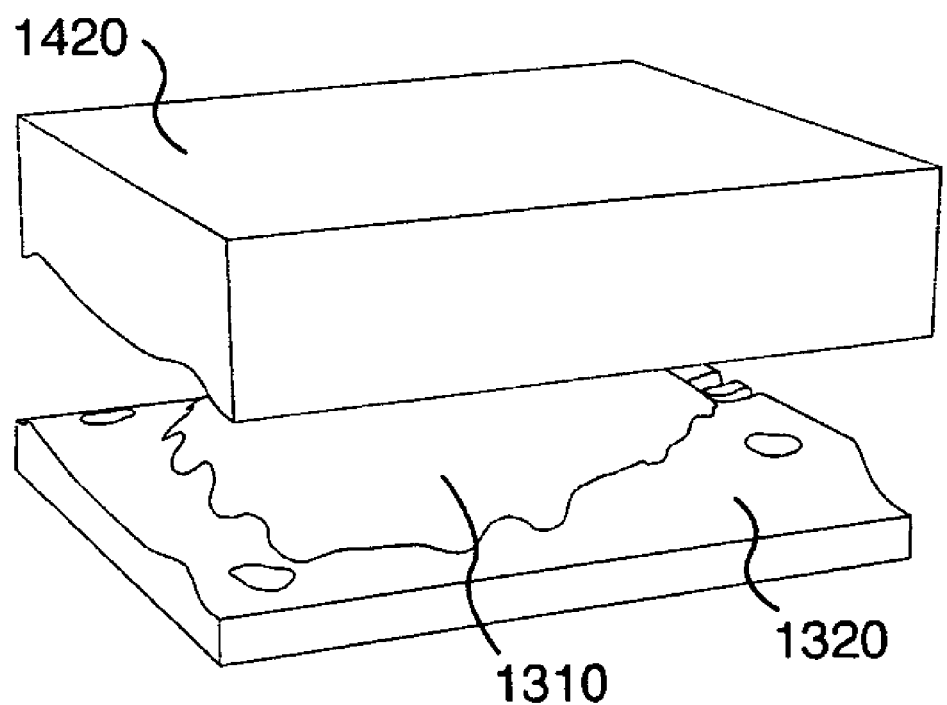
FIG. 14 illustrates an implant embedded into one half of the block that will become the mold and the other half of the mold moving into place according to one embodiment of the present invention.
Figure 15:
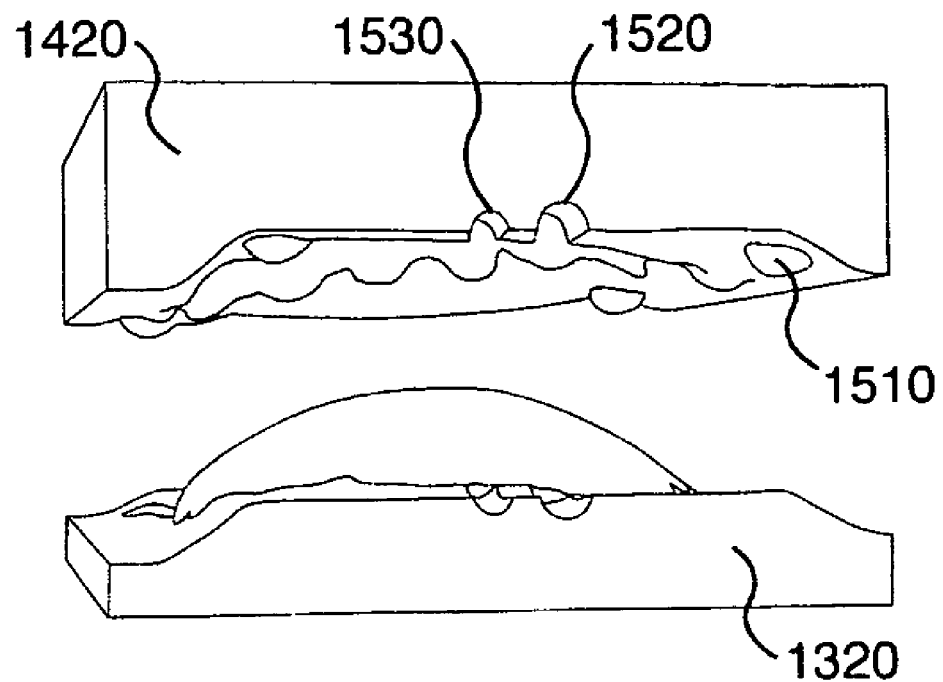
FIG. 15 illustrates a finished mold with the implant subtracted from the two box halves.
Figure 15:
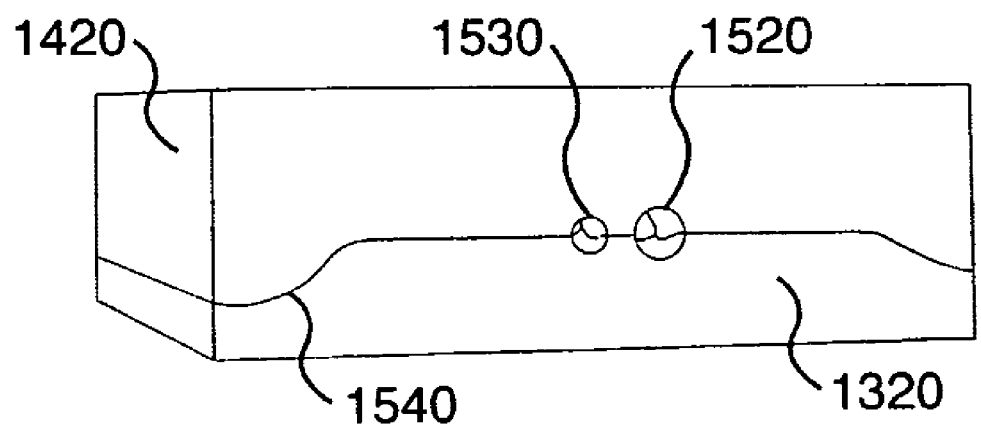

FIG. 12 illustrates a simple block model 1210, showing a potential parting line placement 1220. Simple block model 1210 is a model comprising a solid block volume. FIG. 13 illustrates the implant 1310 embedded into the bottom half 1320 of the block that will become the mold according to one embodiment of the present invention. FIG. 14 illustrates the implant 1310 embedded into the bottom half 1320 of the block that will become the mold and the top half 1420 of the mold moving into place according to one embodiment of the present invention. FIG. 15 illustrates the finished mold with the implant 1310 subtracted from the two mold halves 1320 and 1420, according to one embodiment of the present invention. The bottom illustration of FIG. 14 shows the finished mold put together. Two semi-circular channels may be formed in each of the top half 1420 and bottom half 1320, so that when the mold is closed as in the bottom illustration of FIG. 14, two circular or conical holes 1520, 1530 may used for injection of the final implant material.

The mold as depicted in the embodiment described with reference to FIG. 15 may be derived from the simple block model 1210. After the implant 1310 has been designed, a model of implant 1310 is "subtracted" from the simple block model 1210. By "subtracted," it is meant that the intersection of the volume of the simple block model 1210 and the volume of the implant 1310 model is removed from the simple block model 1210. A parting line 1540 may be designed to transform the resulting simple block model 1210 into a two-part mold model which, when output, will comprise a top half 1420 and a bottom half 1320. A void 1710 exists between the top half 1420 and bottom half 1320 correlating to the volume of the implant 1310 model that was removed from the simple block model 1210.

In the examples illustrated, the parting line 1540 between the top half 1420 and the bottom half 1320 extends toward the bottom half 1320 as it approaches the corner edges of the mold, in order to prevent the top half 1420 from sliding relative to the bottom half 1320 during the implant manufacturing process 250, 350. Indentations 1340 on the lower half 1320 and protrusions 1510 on the top half 1420 may be provided to facilitate the interface of the top half 1420 and the bottom half 1320 and to prevent the top half 1420 from sliding relative to the bottom half 1320 during the implant manufacturing process 250, 350. In one embodiment, the indentations 1340, protrusions 1510, holes 1520 and 1530, and parting line 1540 configuration are designed and incorporated into the computer model of the mold during the steps of creating a two-part mold as a positive model, at block 650, or as a negative model, at block 670. This may be done during the mold design process 230, 330 or the SFF process 240, 340 of the systems of FIGS. 2 and 3.

Figure 16:
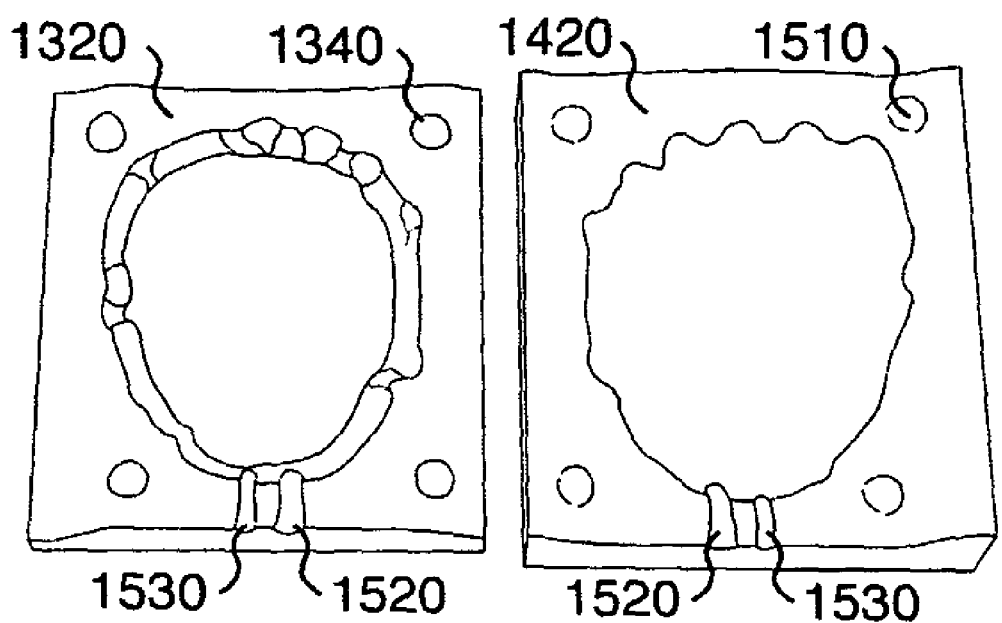
FIG. 16 illustrates the finished mold halves of FIG. 15 in an open position.
Figure 17:
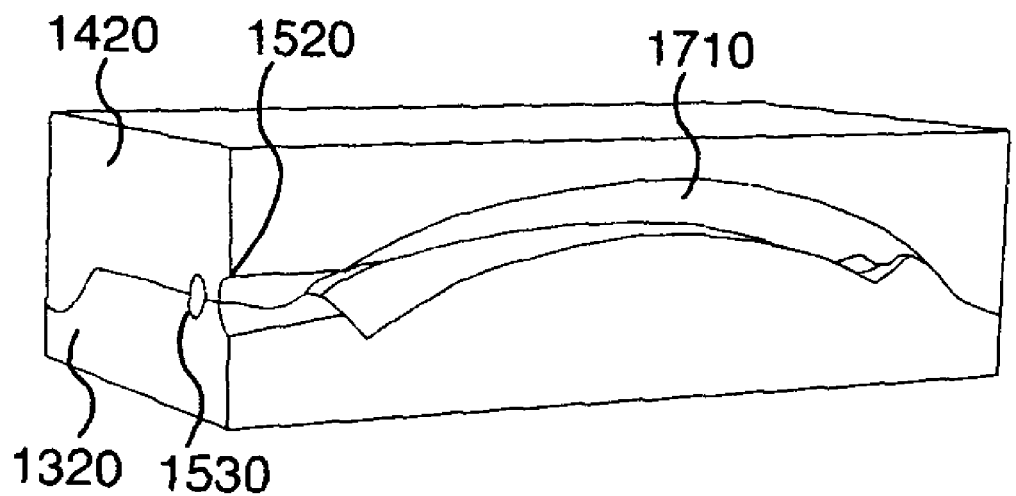
FIG. 17 illustrates a cross section through the mold of FIG. 15 showing the void inside for the implant and the circular injection holes.

FIG. 16 illustrates the finished mold halves, including top half 1420 and bottom half 1320, in an open position. FIG. 17 illustrates a cross section through the mold showing a void 1710 shaped for the formation of the implant and the circular injection holes 1520 and 1530. The holes 1520, 1530 penetrate the outside of the mold and extend to the void 1710. In one embodiment, one of the two holes 1520, 1530 may be used to inject the final implant material and the other of the two holes 1520, 1530 may be used to allow air to escape from the void 1710 as the implant material fills the void 1710.

Figure 18:
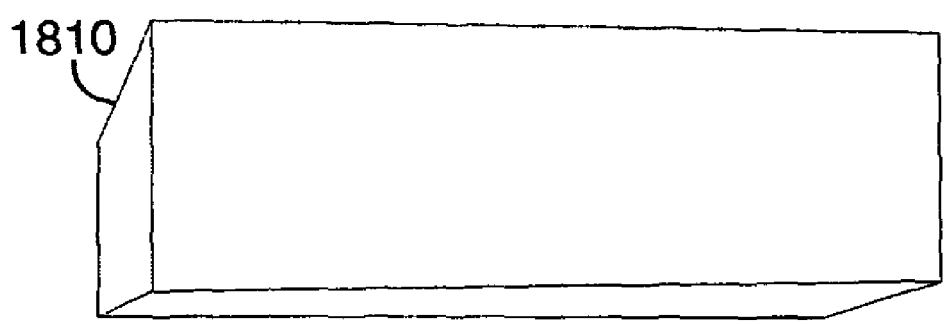
FIG. 18 illustrates lower and upper intermediate block models out of which the intermediate mold may be designed according to one embodiment of the present invention.
Figure 18:
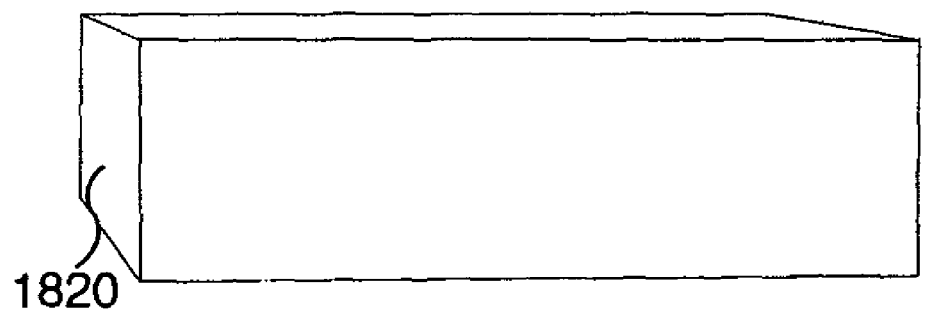
Figure 19:
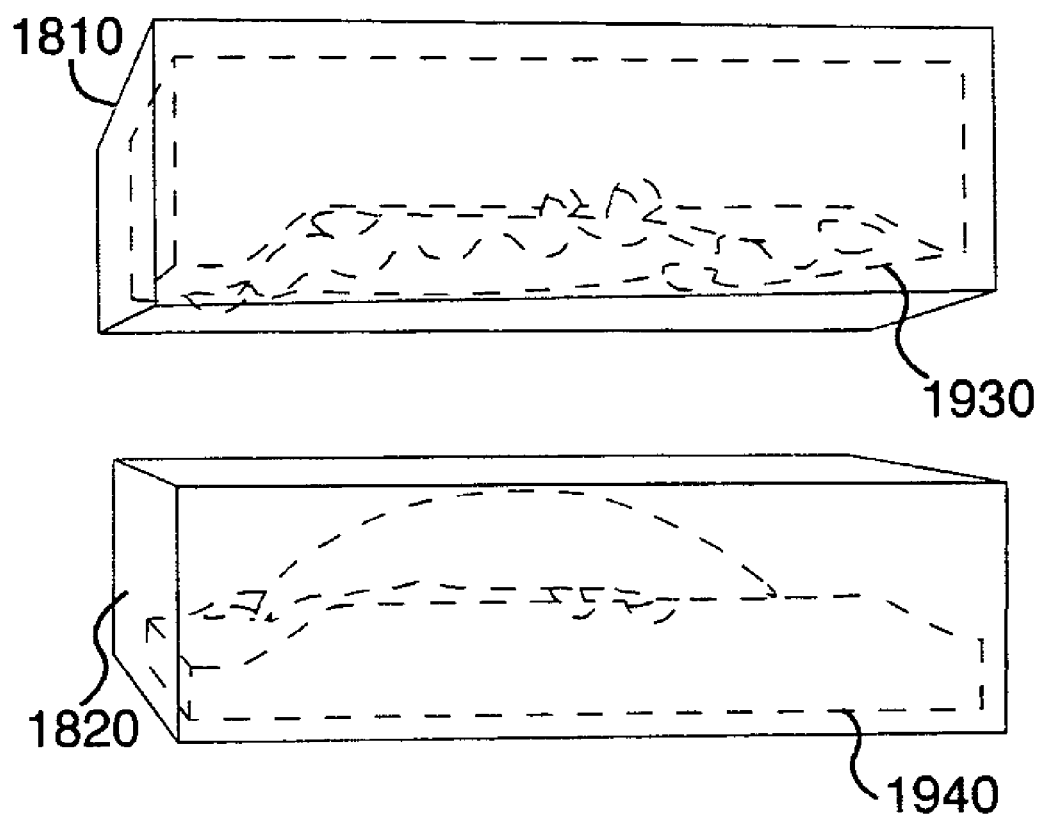
FIG. 19 illustrates making an intermediate mold as a negative object of a model of the finished mold.
Figure 20:
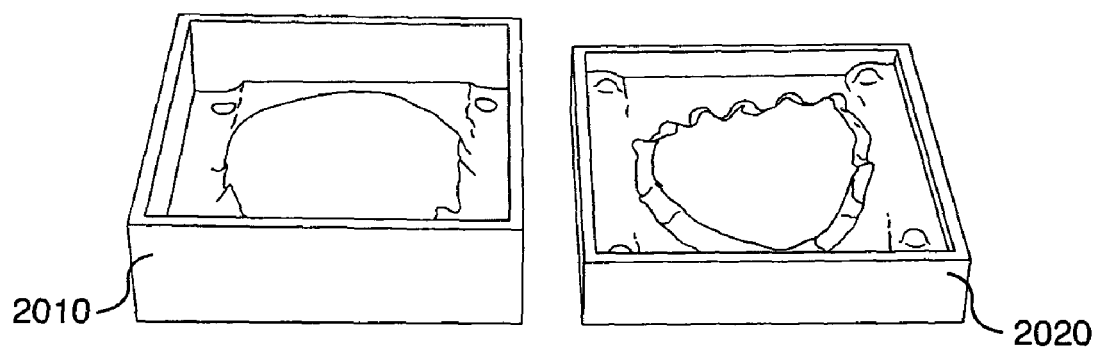
FIG. 20 illustrates a "mold of a mold" concept showing an intermediate mold used to form a positive of the finished mold according to one embodiment of the present invention.

FIGS. 18-21 illustrate creating a mold by first creating a "mold of a mold" (intermediate mold). FIG. 18 illustrates an upper intermediate block model 1810 and a lower intermediate block model 1820. The upper intermediate block model 1810 is a model comprising a solid block volume large enough to surround the top half 1420 of the two-part mold. The lower intermediate block model 1820 is a model comprising a solid block volume large enough to surround the bottom half 1320 of the two-part mold. FIG. 19 illustrates making the mold as a negative object. During the mold design process 330 of the system embodiment described with reference to FIG. 3, a computer is used to subtract a virtual model of a top half shape 1930, which has the same dimensions and characteristics as top half 1420, from the upper intermediate block model 1810. Also during the mold design process 330 of the system of FIG. 3, a computer is used to subtract a virtual bottom half shape 1940, which has the same dimensions and characteristics as bottom half 1320, from a lower intermediate block model 1820. "Subtraction" of two volumes, as used in this context, means removing the intersection of the top half shape 1930 and the upper intermediate block model 1810 from the upper intermediate block model 1810, and also removing the intersection of the bottom half shape 1940 and the lower intermediate block model 1820 from the lower intermediate block model 1820. The resulting forms, when output, are the upper portion of the intermediate mold 2010 and the lower portion of the intermediate mold 2020, as illustrated in FIG. 20.

Figure 21:
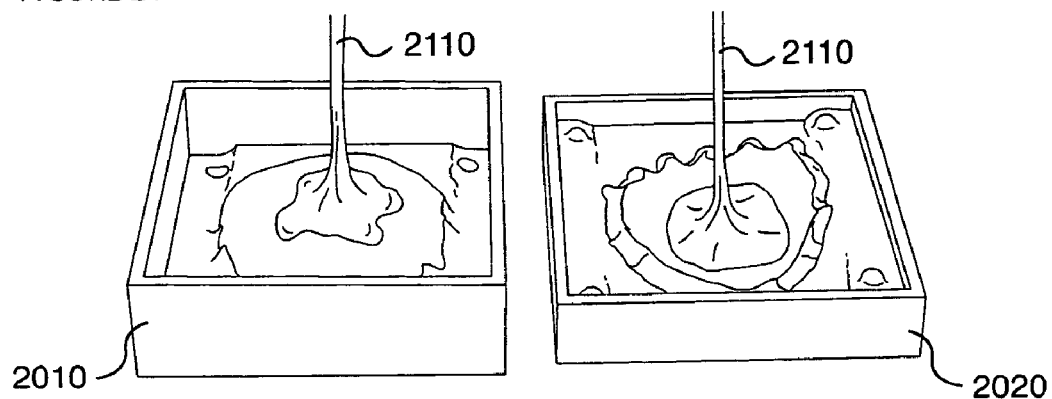
FIG. 21 illustrates pouring a mold material into the intermediate mold.
Figure 22:
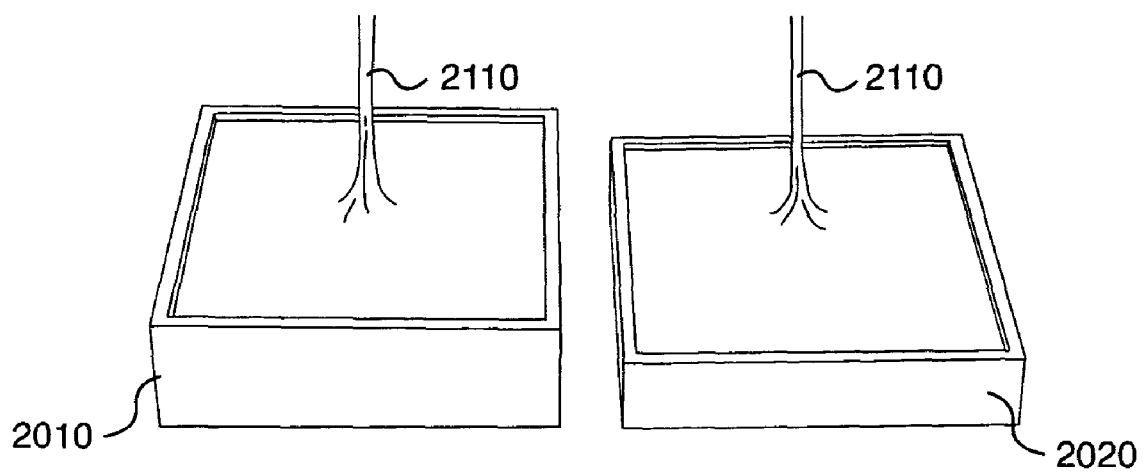
FIG. 22 illustrates the completion of the pouring of the new finished mold.
Figure 23:
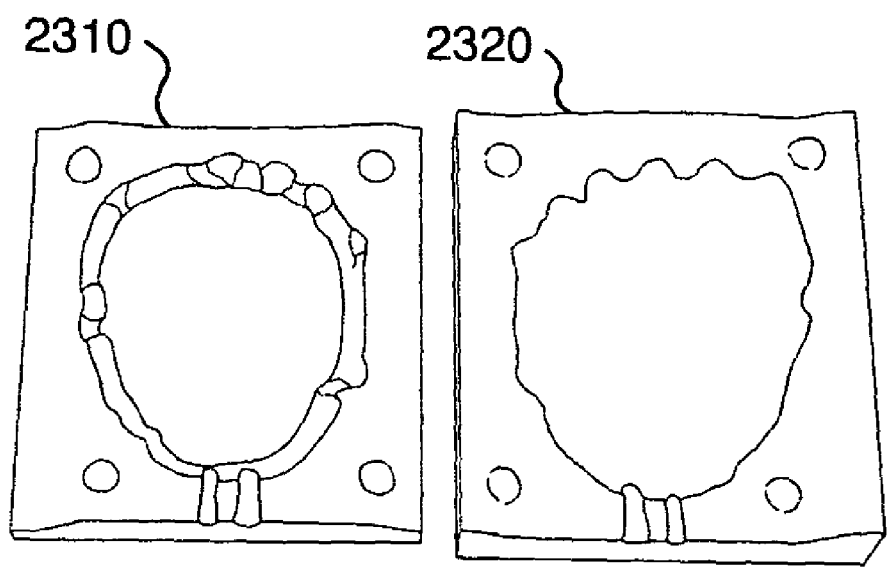
FIG. 23 illustrates the new finished mold produced in a new mold material.

FIG. 20 illustrates the "mold of a mold" concept by showing the upper portion of the intermediate mold 2010 and lower portion of the intermediate mold 2020 that comprise the "mold of a mold" used to make a positive of the actual mold. In FIGS. 21 and 22, mold material 2110 is poured into the upper portion 2010 and lower portion 2020. FIG. 23 illustrates the new mold bottom half 2310 and new mold top half 2320 produced in a new mold material 2110. New mold bottom half 2310 corresponds in shape and size to bottom half 1320, and new mold top half 2320 corresponds in shape and size to top half 1420.

In the foregoing specification and in the provisional patent applications incorporated herein, the invention is described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A system for producing an intermediate mold from which a custom-fit implant mold may be directly manufactured, the system comprising:
   a memory device having stored therein medical image data representing portions of a patient's anatomy; and
   a computer system configured to read the medical image data from the memory device, create a three-dimensional surface reconstruction of the patient's anatomy based on the medical image data, generate a model of the custom-fit implant based on the three-dimensional surface reconstruction, produce a model of a two-part mold based on the model of the custom-fit implant, produce a model of an intermediate mold based on the model of the two-part mold, store the model of the intermediate mold, and output the model of the intermediate mold to a Solid Freeform Fabrication device.

2. The system of claim 1 further comprising a Solid Freeform Fabrication device configured to create the intermediate mold based on the model of the intermediate mold.

3. A system for producing an intermediate mold from which a custom-fit implant mold may be directly manufactured, the system comprising:
   a memory device having stored therein medical image data representing portions of a patient's anatomy;
   a computer system configured to read the medical image data from the memory device, create a three-dimensional surface reconstruction of the patient's anatomy based on the medical image data, generate a model of the custom-fit implant based on the three-dimensional surface reconstruction, produce a model of a two-part mold by producing a negative model of the custom-fit implant, produce a model of an intermediate mold by producing a negative model of the two-part mold, and store the model of the intermediate mold; and
   a Solid Freeform Fabrication device configured to read the model of the intermediate mold and create the intermediate mold based on the model of the intermediate mold.

4. A system for producing an intermediate mold from which a custom-fit implant mold may be directly manufactured, the system comprising:
   a memory device having stored therein medical image data representing portions of a patient's anatomy; and
   a computer system configured to read the medical image data from the memory device, create a three-dimensional surface reconstruction of the patient's anatomy based on the medical image data, generate a model of the custom-fit implant based on the three-dimensional surface reconstruction, produce a model of a two-part mold based on the model of the custom-fit implant, produce a model of an intermediate mold based on the model of the two-part mold, and store the model of the intermediate mold as a Solid Freeform Fabrication file representation.

5. The system of claim 4 further comprising a Solid Freeform Fabrication device configured to receive the Solid Freeform Fabrication file representation and create the intermediate mold based on Solid Freeform Fabrication file representation.

* * * * *

UNITED STATES PATENT AND TRADEMARK OFFICE
CERTIFICATE OF CORRECTION

| | | |
|---|---|---|
| PATENT NO. | : 8,086,336 B2 | Page 1 of 1 |
| APPLICATION NO. | : 10/957498 | |
| DATED | : December 27, 2011 | |
| INVENTOR(S) | : Andrew Michael Christensen | |

It is certified that error appears in the above-identified patent and that said Letters Patent is hereby corrected as shown below:

In Column 14, line 45, insert the word --the-- before the words "Solid Freeform Fabrication"

Signed and Sealed this
Twentieth Day of March, 2012

David J. Kappos
*Director of the United States Patent and Trademark Office*